United States Patent [19]
Levere et al.

[11] Patent Number: 5,217,997
[45] Date of Patent: Jun. 8, 1993

[54] USE OF L-ARGININE IN THE TREATMENT OF HYPERTENSION AND OTHER VASCULAR DISORDERS

[76] Inventors: Richard D. Levere, 5 Seymour Pl. W., Armonk, N.Y. 10504; Nader G. Abraham, 143 Charter Cir., Ossining, N.Y. 10562; Michel L. Schwartzman, 415 Old Country Rd., Elmsford, N.Y. 10523; Pavel Martasek, 60 Hillcrest Rd., Hartsdale, N.Y. 10530

[21] Appl. No.: 873,892

[22] Filed: Apr. 24, 1992

Related U.S. Application Data

[63] Continuation of Ser. No. 513,895, Apr. 24, 1990, abandoned, which is a continuation-in-part of Ser. No. 462,638, Jan. 9, 1990, abandoned.

[51] Int. Cl.$^5$ ............................................ A61K 31/195
[52] U.S. Cl. ..................................................... 514/565
[58] Field of Search .......................................... 514/565

[56] References Cited

U.S. PATENT DOCUMENTS 3,542,929  11/1970  Roberts .............................. 514/565

OTHER PUBLICATIONS

Lais, et al., "Mechanism of Vascular Hyperresponsiveness in the Spontaneously Hypertensive Rat," *Cir. Res.*, 36/37: Suppl. 1, I-216, to I-222 (1975).

Pinto, et al., "Arachidonic Acid-Induced Endothelial-Dependent Relaxations of Canine Coronary Arteries: Contribution of a Cytochrome P-450-Dependent Pathway," *J. Pharmacol. Exp. Therap.*, vol. 240, No. 3, 856-863 (1987).

Luscher, et al., "Endothelium-Dependent Responses in Cartoid and Renal Arteries of Normotensive and Hypertensive Rats," *Hypertension*, vol. 11, No. 6, Part 2, 573-578 (1988).

Sacerdoti, et al., "Treatment with Tin Prevents the Development of Hypertension in Spontaneously Hypertensive Rats," *Science*, vol. 243, 388-390 (1989).

Martasek, et al., "Heme Arginate Lowers Blood Pressure in Spontaneously Hypertensive Rats," *Clin. Res.*, vol. 37, 553A (1989).

Merrick, et al., "Alternations in Hepatic Microsomal Drug Metabolism and Cytochrome P450 Proteins in Spontaneously Hypertensive Rats," *Pharmacol.* 30, 129-135 (1985).

Sacerdoti, et al., "Renal Cytochrome P450-Dependent Metabolism of Arachidonic Acid in Spontaneously Hypertensive Rats," *Biochem. Pharmacol.*, vol. 37, No. 3, 521-527 (1988).

Kappas, et al., "Control of Heme Metabolism with Synthetic Metalloprophyrins," *J. Clin. Invest.*, vol. 77, 335-339 (1986).

Simionatto, et al., "Studies of the Mechanism of Sn--Protoporphyrin Suppression and Hyperbilirubinemia: Inhibition of Heme Oxidation and Bilirubin Production," *J. Clin. Invest.*, vol. 75, 513-521 (1985).

Escalante, et al., "19(S)Hydroxyeicosatetraenoic Acid is a Potent Stimulator of Renal Na$^+$-K$^+$-ATPase," *Biochem. & Biophys. Res. Commun.*, vol. 152, No. 3, 1269-1273 (1988).

(List continued on next page.)

*Primary Examiner*—Allen J. Robinson
*Attorney, Agent, or Firm*—Burns, Doane, Swecker & Mathis

[57] ABSTRACT

A method for treating a high vascular resistance disorder in a mammal by administering to a mammalian organism in need of such treatment a sufficient amount of L-arginine or pharmaceutically acceptable salt thereof to treat a high vascular resistance disorder. The L-arginine is typically administered in the range of about 1 mg to 1500 mg per day. High vascular resistance disorders include hypertension, primary or secondary vasospasm, angina pectoris, cerebral ischemia and preeclampsia. Also disclosed is a method for preventing or treating bronchial asthma in a mammal by administering to a mammalian organism in need of such prevention or treatment a sufficient amount of L-arginine to prevent or treat bronchial asthma.

19 Claims, 3 Drawing Sheets

OTHER PUBLICATIONS

Escalante, et al, "Vasoactivity of 20-Hydroxyeicosatetraenoic Acid is Dependent on Metabolism by Cyclooxygenase," *J. Pharmacol. Exp. Therap.*, vol. 248, No. 1, 229–232 (1989).

Furchgott, et al., "The Role of Endothelium in the Responses of Vascular Smooth Muscle to Drugs," *Ann. Rev. Pharmacol. Toxicol.*, 24, 175–197 (1984).

Palmer, et al., "Vascular Endothelial Cells Synthesize Nitric Oxide from L-Arginine," *Nature*, vol, 333, 664–666 (1988).

Ignarro, et al., "Endothelium-Derived Nitric Oxide: Actions and Properties," *FASEB J.*, vol. 3, 31–36 (1989).

Kordac, et al., "Changes of Myocardial Functions in Acute Hepatic Porphyrias, Role of Heme Arginate Administration," *Ann. Med.*, 21, 273–276 (1989).

Rees, et al., "Role of Endothelium-derived Nitric Oxide in the Regulation of Blood Pressure," *Proc. Natl. Acad. Sci. USA*, vol. 86, 3375–3378 (1989).

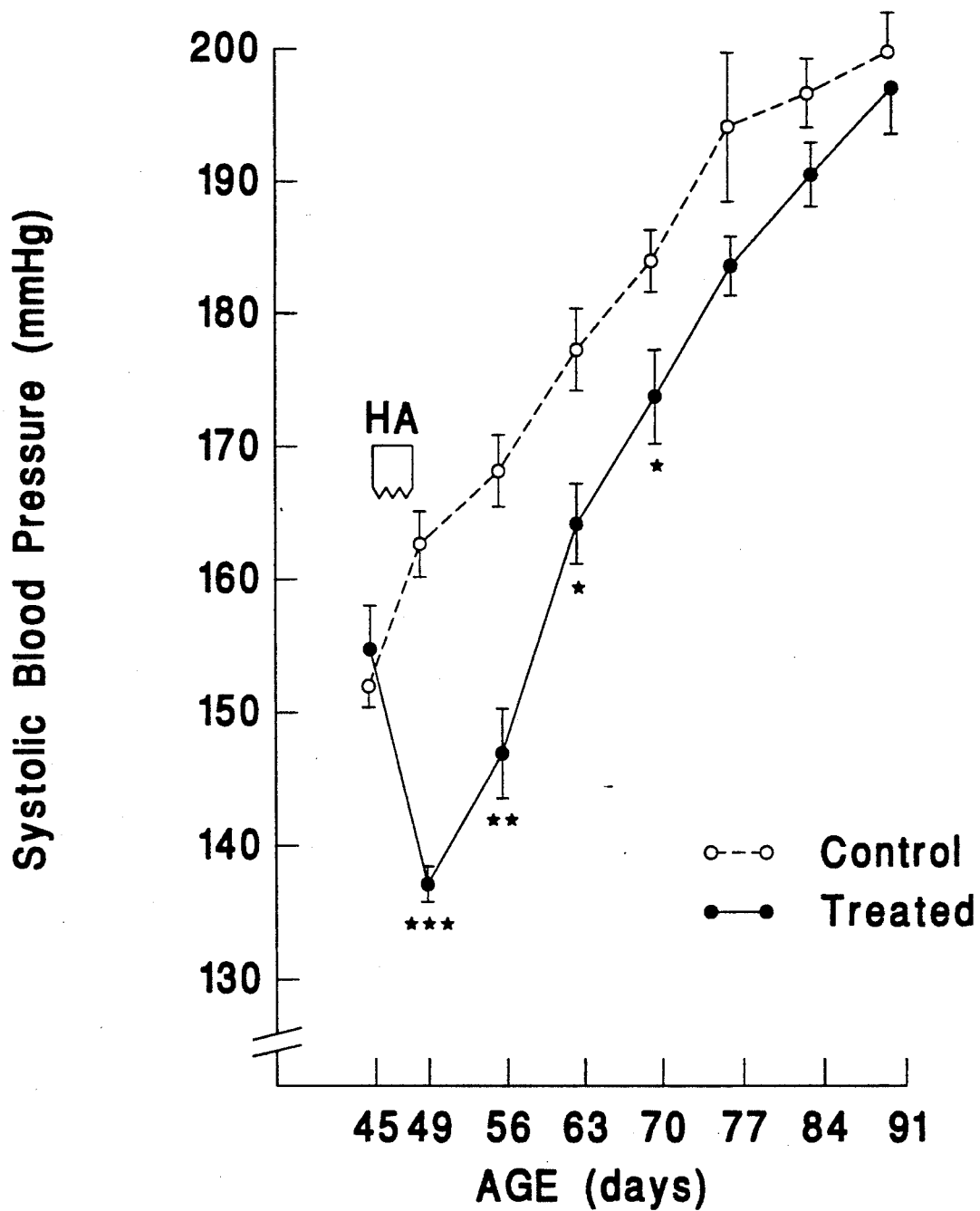

USE OF L-ARGININE IN THE TREATMENT OF HYPERTENSION AND OTHER VASCULAR DISORDERS

This application is a continuation of application Ser. No. 07/513,895, filed Apr. 24, 1990 now abandoned, which is a continuation-in-part of U.S. Ser. No. 07/462,638, filed Jan. 9, 1990, now abandoned.

BACKGROUND OF THE INVENTION

1. Field of the Invention

The present invention relates to a method of using L-arginine or pharmaceutically acceptable salts thereof in the treatment of hypertension and other high vascular resistance disorders. High vascular resistance disorders include primary or secondary vasospasm, angina pectoris, cerebral ischemia and preeclampsia of pregnancy. The present invention is also concerned with a method of preventing or treating bronchial asthma using L-arginine or a pharmaceutically acceptable salt thereof.

2. Description of the Prior Art

The disposition of hypertensive patients to develop vascular disease which leads to increased mortality from stroke and myocardial infarction is a major problem in the western world. The development of hypertension can relate to abnormalities in the production or activities of vasoactive substances. Alteration in the responsiveness to both vasoconstrictors and vasodilators has been well documented in spontaneous hypertensive rats, the most frequently used animal model for the study of human essential hypertension. Thus, an increase in the contractile response of vascular smooth muscle of spontaneous hypertensive rats to vasoconstrictors such as norepinephrine as noted by Lais et al, "Mechanism of Vascular Hyperresponsiveness in the Spontaneously Hypertensive Rat", Cir. Res., 36/37: Suppl. 1, I-216 to I-222 (1975), and a decrease in the relaxant response to vasodilators such as acetylcholine, nitrovasodilators, prostaglandin and other arachidonic acid metabolites as noted by Pinto et al, "Arachidonic Acid-Induced Endothelial-Dependent Relaxations of Canine Coronary Arteries: Contribution of a Cytochrome P-450-Dependent Pathway", *J Pharmacol. Exp. Therap.*, 240, 856–863 (1987) and Luscher et al, "Endothelium-Dependent Responses in Carotid and Renal Arteries of Normotensive and Hypertensive Rats", *Hypertension*, 11, 573–578 (1988), may contribute overall to the development of high blood pressure.

It has also been demonstrated that cytochrome P-450-arachidonate metabolism is increased in the kidney of young spontaneous hypertensive rats and a selective reduction in the formation of these metabolites via induction of heme degradation with $SnCl_2$ caused a marked decrease in blood pressure as noted by Sacerdoti et al, "Treatment with Tin Prevents the Development of Hypertension in Spontaneously Hypertensive Rats", *Science*, 243, 388–390 (1989). Martasek et al, "Heme Arginate Lowers Blood Pressure in Spontaneous Hypertensive Rats", *Clin. Res.*, 37, 553A (1989) also noted that other heme oxygenase inducers such as heme arginate have been demonstrated to be an inducer of heme oxygenase causing reduction of renal P-450 and a decrease in blood pressure in young spontaneous hypertensive rats. The blood pressure lowering effect of heme arginate could be attributed to the heme component. The heme effect may be due to an induction of heme oxygenase, since it is blocked by an inhibitor of heme oxygenase.

The relaxation of vascular smooth muscle in response to many substances is typically endothelium-dependent and mediated by endothelium-derived relaxing factors as noted by Furchgott et al, "The Role of Endothelium in the Responses of Vascular Smooth Muscle to Drugs", *Ann. Rev. Pharmacol. Toxicol.*, 24, 175–197 (1984). One of the endothelium-derived relaxing factors has been recently identified as nitric oxide by Palmer et al, "Vascular Endothelial Cells Synthesize Nitric Oxide from L-arginine", *Nature*, 333, 664–666 (1988); and Ignarro et al, "Endothelium-Derived Nitric Oxide: Actions and Properties", *FASEB J.*, 3, 31–36 (1989). Nitric oxide elicits vasodilation by increasing the formation of c-GMP following direct interaction with the heme component of soluble guanylate cyclase (Ignarro et al, supra).

An increase in hepatic and renal cytochrome P-450 content and its related drug metabolizing enzyme systems has been demonstrated in spontaneous hypertensive rats as noted by Merrick et al, "Alterations in Hepatic Microsomal Drug Metabolism and Cytochrome P450 Proteins in Spontaneously Hypertensive Rats", *Pharmacol.*, 30, 129–135 (1985) and Sacerdoti et al, "Renal Cytochrome P450-Dependent Metabolism of Arachidonic Acid in Spontaneously Hypertensive Rats", Biochem. Pharmacol., 37, 521–527 (1988). More recently Sacerdoti et al demonstrated that abnormalities of renal function in young spontaneous hypertensive rats may be a functional expression of an alteration in renal cytochrome P-450-dependent metabolism of arachidonic acid. Cytochrome P-450 levels are regulated by the availability of cellular heme which in turn is controlled by the levels of heme oxygenase which is the controlling enzyme in the metabolism of heme to bilirubin. Induction of heme oxygenase by heavy metals such as $SnCl_2$ results in a depletion of renal cytochrome P-450 as described by Kappas et al, "Control of Heme Metabolism with Synthetic Metalloprophyrins", *J. Clin. Invest.*, 77, 335–339 (1986) and Simionatto et al, "Studies on the Mechanism of Sn-Protoporphyrin Suppression and Hyperbilirubinemia: Inhibition of Heme Oxidation and Bilirubin Production", *J. Clin. Invest.*, 75, 513–521 (1985).

Furthermore, it has recently been demonstrated by Escalante et al, "19(S)Hydroxyeicosatetraenoic Acid is a Potent Stimulatior of Renal $Na^+$-$K^+$-ATPase", *Biochem. Biophys. Res. Commun.*, 152, 1269–1273 (1988) and Escalante et al, "Vasoactivity of 20-Hydroxyeicosatetraenoic Acid is Dependent on Metabolism by Cyclooxygenase", *J. Pharmacol. Exp. Therap.*, 248, 229–232 (1989) that arachidonic acid metabolites of cytochrome P-450 $\omega/\omega$-1 hydroxylases, 19(S)-HETE (hydroxyeicosatetragenoic acid) and 20-HETE is a potent renal $Na^+$-$K^+$-ATPase stimulator and 20-HETE is a vasoconstrictor.

An acute attack of acute intermittent porphyria, a disease caused by inborn errors of porphyrin metabolism, is a life threatening condition, often characterized by agonizing abdominal pain, paresis and frequently accompanied by hypertension. The exact pathogenesis of hypertension in an acute porphyric attack is not well understood. Currently, hemin in the form of heme arginate is used in Europe in the treatment of acute attacks of acute intermittent porphyria so as to normalize the levels of "free" heme and thereby decrease the induced levels of delta-aminolevulinic acid synthetase, an enzyme under negative feedback control by unbound or "free" heme. Kordac et al, "Changes of Myocardial Functions in Acute Hepatic Porphyrias. Role of Heme Arginate Administration", *Ann. Med.*, 21, 273-276 (1989) disclosed the use of heme arginate in the treatment of acute hepatic porphyria. Heme arginate was administered to those patients because it was speculated that acute hypoxia occurs in a porphyrin crisis due to lack of heme. The arginate was used as a way to solubilize the heme for administration to the patient.

It has long been thought that the source of nitric oxide and other nitroso species in animal tissues is L-arginine. Indeed, recent studies have demonstrated that cultured endothelial cells transform L-arginine to the nitroso species, thus supporting the suggestion that L-arginine is a physiological precursor of endothelium-derived nitric acid. Ignarro et al, supra.

Rees et al, "Role of Endothelium-derived Nitric Oxide in the Regulation of Blood Pressure", *Proc. Natl. Acad. Sci. USA*, 86, 3375-3378 (1989) used N-monomethyl-L-arginine to investigate the role of nitric oxide in the regulation of blood pressure in the anesthetized rabbit. The authors concluded that N-monomethyl-L-arginine caused a dose-dependent increase in mean arterial blood pressure. It was also determined that the administration of L-arginine abolished the inhibition of N-monomethyl-L-arginine within fifteen minutes. Their findings further suggested that there is a continuous utilization of L-arginine for the enzymatic formation of nitric oxide by resistance arteries and provides the first evidence that nitric oxide formation contributes to the regulation of blood pressure. No studies were undertaken to test whether the administration of L-arginine could affect blood pressure and the authors specifically stated that they did not believe that L-arginine directly affected blood pressure.

All investigations into the action of nitric oxide and L-arginine ended there. There nevertheless remained a long-felt need in the art for a way of treating a variety of vascular diseases including hypertension. In addition, there remains a long-felt need in the art for a way to prevent or treat bronchial asthma which involves the narrowing of large and small airways due to spasm of bronchial smooth muscle.

SUMMARY OF THE INVENTION

Surprisingly, the present inventors now find that the levorotatory form of arginine is useful in the treatment of high vascular resistance disorders including hypertension, primary or secondary vasospasm, angina pectoris, cerebral ischemia and preeclampsia of pregnancy in a mammalian organism, such as a human.

In one aspect, the present invention thus provides a method for treating hypertension in a mammalian organism by administering to a mammalian organism in need of such treatment a sufficient amount of L-arginine or pharmaceutically acceptable salt thereof to treat hypertension.

In another aspect, the invention thus provides a method for treating vasospasm in a mammalian organism in need of such treatment a sufficient amount of L-arginine or pharmaceutically acceptable salt thereof to treat vasospasm.

In a further aspect, the present invention provides a method for treating angina pectoris in a mammalian organism by administering to a mammalian organism in need of such treatment a sufficient amount of L-arginine or pharmaceutically acceptable salt thereof to treat angina pectoris.

In yet another aspect, the present invention provides a method for treating cerebral ischemia in a mammalian organism by administering to a mammalian organism in need of such treatment a sufficient amount of L-arginine or pharmaceutically acceptable salt thereof to treat cerebral ischemia.

In an additional aspect, the present invention provides a method for treating preeclampsia in a mammalian organism by administering to a mammalian organism in need of such treatment a sufficient amount of L-arginine or pharmaceutically acceptable salt thereof to treat preeclampsia.

A further embodiment of the present invention involves a method for treating bronchial asthma in a mammalian organism by administering to a mammalian organism in need of such treatment a sufficient amount of L-arginine or pharmaceutically acceptable salt thereof to treat bronchial asthma.

Other objects and advantages of the present invention will be apparent from the following description.

BRIEF DESCRIPTION OF THE FIGURES

FIG. 3 is a graph of the long-term effect of heme arginate on systolic blood pressure when 45-week-old spontaneous hypertensive rats were injected with heme arginate (15 mg/kg) for four consecutive days and the control spontaneous hypertensive rats were injected only with the vehicle.

DETAILED DESCRIPTION OF THE PREFERRED EMBODIMENTS

Figure 1:
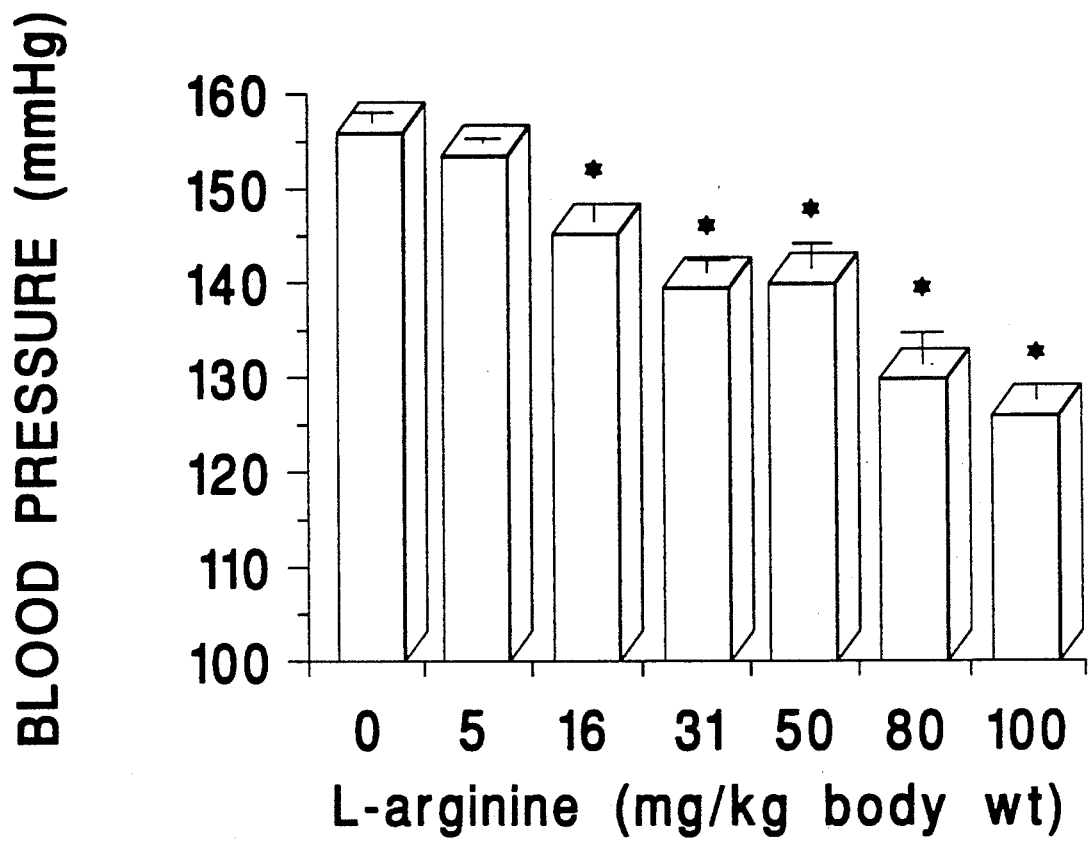
FIG. 1 is a bar chart showing that L-arginine caused a dose-dependent decrease in blood pressure of spontaneous hypotensive rats.

Arginine, 2-amino-5-guanidinovaleric acid, is a basic amino acid with a positively charged guanidinium group. The IUPAC abbreviation is Arg. Arginine can be depicted as follows:

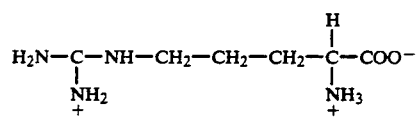

Arginine is considered to be a semi-essential amino acid. It can be synthesized in animal tissues at a rate sufficient for maintenance in the adult but not rapidly enough to support growth in the young animal. It is thus an essential amino acid for growth but not for maintenance.

In the mammalian body, arginine takes part in the formation of urea yielding ornithine. Arginine may be synthesized in the mammalian body from alpha-ketoglutaric acid, glutamic acid or proline.

L-arginine can be used in the treatment of a number of high vascular resistance disorders including hypertension, primary or secondary vasospasm, angina pectoris, cerebral ischemia and preeclampsia of pregnancy (toxemia). Each of those high vascular resistance disorders are well-known in the art.

Hypertension is characterized by persistently high arterial blood pressure. Various criteria for its threshold have been suggested ranging from 140 mm Hg systolic and 90 mm Hg diastolic to as high as 200 mm Hg systolic and 110 mm Hg diastolic. Hypertension may have no known cause (essential or idiopathic hypertension) or be associated with other primary diseases (secondary hypertension).

Vasospasm refers to a spasm of the blood vessels, resulting in a decrease in their caliber. Primary vasospasm can be described as a cold sensitivity of the Raynaud's type without an underlying disease. Secondary vasospasm generally refers to cold sensitivity of the Raynaud's type secondary to an associated disease such as lupus, scleroderma, certain medication, chronic arterial disease, dysprotenemias and the like.

Angina pectoris is a paroxysmal thoracic pain oftentimes accompanied by a feeling of suffocation and impending death, due, most often, to anoxia of the myocardium and precipitated by effort or excitement.

Cerebral ischemia is a deficiency of blood in the brain, due to functional constriction or actual obstruction of a blood vessel.

Preeclampsia is a toxemia of late pregnancy characterized by hypertension, edema and proteinuria.

Bronchial asthma is a reversible obstructive lung disorder characterized by increased responsiveness of the airways. Bronchial asthma attacks are characterized by narrowing of large and small airways due to spasm of bronchial smooth muscle, edema and inflammation of the bronchial mucosa and production of tenacious mucus. The role of inflammation in the perpetuation of the abnormal airway responses (late-phase reaction) is only now being appreciated. Airways obstruction causes hypoventilation in some lung areas, and continued blood flow to these area leads to a ventilation/perfusion imbalance resulting in hypoxema. Arterial hypoxemia is almost always present in attacks severe enough to require medical attention. Hyperventilation occurs early in the attack. As the attack progresses, the patient's capacity to compensate by hyperventilation of unobstructed areas of the lung is further impaired by more extensive airways narrowing and muscular fatigue. Arterial hypoxema worsens and can lead to respiratory acidosis.

In addition to L-arginine, any salt of L-arginine is suitable in the practice of the present invention. Such salts include 2,4-bisglyco-deuteroporphyrin L-arginate, 2,4-sulfonedeuteroporphyrin L-arginate, heme-L-arginate, L-arginine hydrochloride and the like. L-arginine hydrochloride is the preferred salt in the practice of the present invention.

Additional suitable anions for such a salt of L-arginine include bromide, fluoride, iodide, borate, hypobromite, hypochlorite, nitrite, nitrate, hyponitrite, sulfate, disulfate, sulfite, sulfonate, phosphate, diphosphate, phosphite, phosphonate, diphosphonate, perchlorate, perchlorite, oxalate, malonate, succinate, lactate, carbonate, bicarbonate, acetate, benzoate, citrate, tosylate, permanganate, manganate, propanolate, propanoate, ethandioate, butanoate, propoxide, chromate, dichromate, selenate, orthosilicate, metasilicate, pertechnetate, technetate, dimethanolate, dimethoxide, thiocyanate, cyanate, isocyanate, 1,4-cyclohexanedithiolate, oxidobutanoate, 3-sulfidocyclobutane-1-sulfonate, 2-(2-carboxylatoethyl)-cyclohexanecarboxylate, 2-amino-4-(methylthio)-butanoate and the like. The suitable cation for most salts is hydrogen, however, other cations such as sodium, potassium and the like would be acceptable in the preparation of such a salt. It would be advantageous if the specific salt form selected allowed a pH close to neutral.

Heme-L-arginate is a pharmacological agent with the ability to induce heme oxygenase. It is a stable compound bonding one molecule of heme to three molecules of arginine and forms a high spin-type compound. The half-life of heme arginate in humans is $10.8 \pm 0.6$ hours with a volume of distribution of $33.7 \pm 0.34$ liter.

The precise amount of L-arginine suitable for use in the practice of the present invention will vary depending on the condition for which the drug is administered, the size and kind of the mammal, as well as the specific form, i.e., salt, selected. Generally speaking, L-arginine is intended for administration to humans.

The typical effective amount of L-arginine or pharmaceutically acceptable salt thereof to reduce vascular resistance would be in the range of about 1 mg to about 1500 mg per day, more preferably, about 10 mg to about 400 mg. The preferred amount of L-arginine for use in the treatment of hypertension is about 1 mg to about 1500 mg per day, more preferably, about 10 mg to about 400 mg. Likewise, the typical effective amount of L-arginine or pharmaceutically acceptable salt thereof to prevent or treat bronchial asthma would be in the range of about 1 mg to about 1500 mg per day, more preferably about 10 mg to 400 mg per day. Pediatric compositions would typically contain proportionally less of the active ingredient.

L-arginine or a salt thereof may be administered to a mammalian organism by any route of administration. Suitable routes would, of course, include oral, parenteral, topical, and the like. The oral dosage form is preferred.

Preferably, the L-arginine is formulated with any suitable nontoxic pharmaceutically acceptable inert carrier material. Such carrier materials are well known to those skilled in the art of pharmaceutical formulations. For those not skilled in the art, reference is made to the text entitled, "REMINGTON'S PHARMACEUTICAL SCIENCES".

In a typical preparation for oral administration, e.g., tablet or capsule, the active ingredient, i.e., L-arginine, may be combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents may be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate.

If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g., an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. Such compositions should preferably contain at least 0.1% of active components; generally, the active ingredients will be between about 2% to about 60% of the weight of the unit.

Likewise, injectable (injectable, intramuscular, intraperitoneal and the like) and topical, especially the newer topical "patch" forms of L-arginine, may be prepared by any method known in the art.

The L-arginine may also be formulated as a long-acting preparation to minimize the intervals between administration. Such long-acting formulations would be applicable with virtually all known routes of administration and such preparations may be formulated by techniques known in the art.

The mechanism of the blood pressure lowering effect of L-arginine is still unclear. However, while not wishing to be bound by any theory, the observation that spontaneous hypertensive rats have a diminished endothelial-dependent relaxation response and that L-arginine may be the physiological precursor of the most powerful endothelial-derived releasing factor, nitric oxide, may suggest that administration of L-arginine to spontaneous hypertensive rats increases the formation of nitric oxide and contributes to an overall decrease in peripheral vascular resistance, and therefore causes a reduction in blood pressure. It is also possible that there is a direct effect on renal hemodynamics. Likewise, with respect to bronchial asthma, it is speculated that the administration of L-arginine results in the relaxation of bronchial smooth muscle.

While the present invention is described above in connection with preferred or illustrative embodiments, those embodiments are not intended to be exhaustive or limiting of the invention. Rather, the invention is intended to cover all alternatives, modifications and equivalents included within its spirit and scope, as defined by the appended claims.

EXAMPLE 1

Administration of L-arginine Hydrochloride

Male spontaneous hypertensive rats and Wistar Kyoto rats were purchased from Charles River (Wilmington, Mass.) and were fed and housed under identical conditions for at least five days before use. The rats were caged in groups of three with food and water ad libitum under an artificial light-dark cycle of twelve hours.

L- and D-arginine hydrochloride were obtained from Aldrich (Milwaukee, Wis.). Forty-five-day-old spontaneous hypertensive rats were injected with L-arginine hydrochloride, 5, 16, 50, 80, 100 and 500 mg/kg body weight, or D-arginine-hydrochloride, 80 and 100 mg/kg body weight, intraperitoneally, in a final volume of 1.0 ml buffered saline for four consecutive days. The control spontaneous hypertensive rats and Wistar Kyoto rats were injected with saline. Forty-five day old Wistar Kyoto strain rats were injected with 50 mg/kg body weight of L-arginine hydrochloride for four days. Each group consisted of four or five experimental animals. Blood pressure from the tail was measured before the first injection and twenty-four hours after the last arginine administration. Blood pressure was measured with anesthesia, using a pletysmograph.

Results are expressed as the means ±SEM. A two-way analysis of variance was performed to compare blood values between control, L-arginine and D-arginine treated spontaneous hypertensive rats. Specific differences between groups were tested by the Newman-Keuls test. The null hypothesis was rejected when the p value was less than 0.05.

The blood pressure of 7-week-old spontaneous hypertensive rats and Wistar Kyoto rats was monitored before and after administration of L- and D-arginine. As seen in FIG. 1, L-arginine caused a dose-dependent decrease in blood pressure of 7-week-old spontaneous hypertensive rats. At a dose as low as 16 mg/kg body weight, L-arginine lowered blood pressure by 10 mm Hg (p=7). The maximal effect of L-arginine, a decrease of 30 mm Hg, was achieved at 100 mg/kg body weight. Higher doses of L-arginine did not lower blood pressure further.

Figure 2:
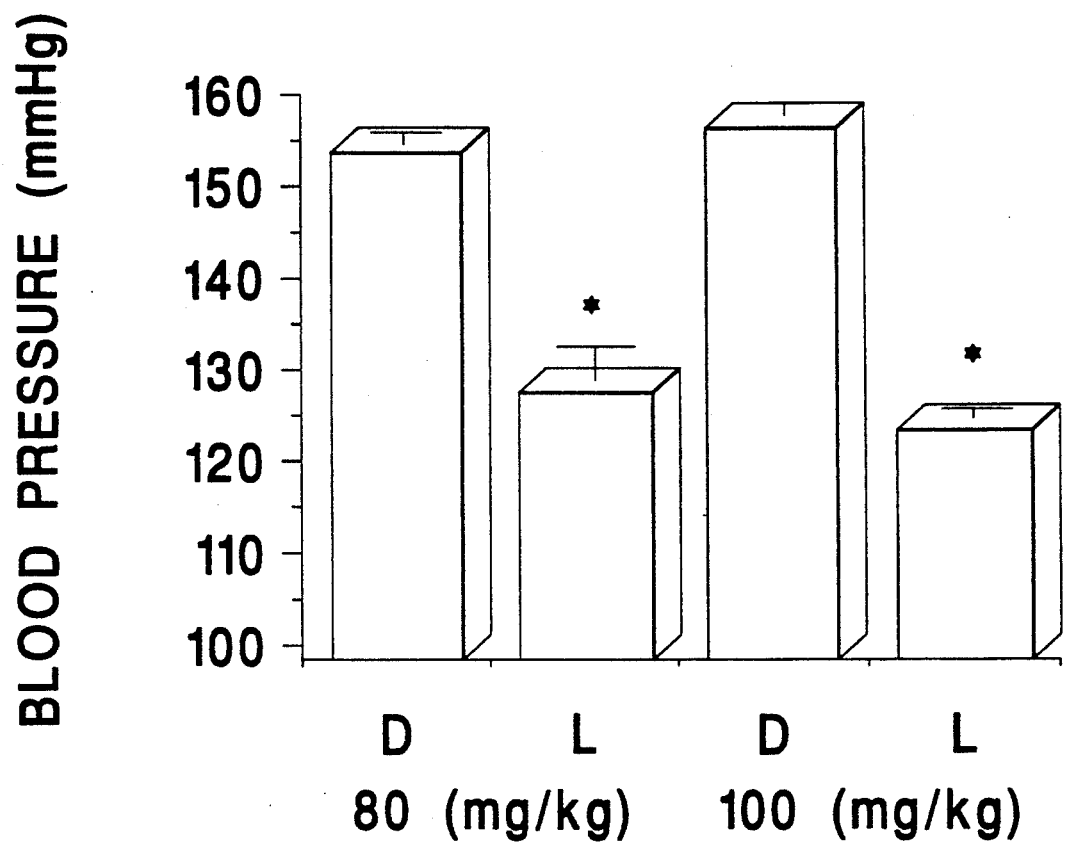
FIG. 2 is a bar chart showing that D-arginine at a dose of 80 and 100 mg/kg did not effect the blood pressure of spontaneous hypotensive rats.

The effect of D-arginine on blood pressure of 7-week-old spontaneous hypertensive rats is shown in FIG. 2. D-arginine administered at a dose of 80 and 100 mg/kg body weight for four days had no effect on blood pressure of spontaneous hypertensive rats. Furthermore, D-arginine did not alter blood pressure at concentrations lower than 80 mg/kg body weight. Neither L-arginine nor D-arginine had any effect on blood pressure of the age-matched Wistar Kyoto rats. For example, blood pressure of 7-week-old Wistar Kyoto rats remained unchanged following four days of treatment with L-arginine (50 mg/kg body weight), 122.3±1.3 mm Hg vs. 124.5±1.7 mm Hg for control and treated, respectively, n=3.

The results described in this study clearly demonstrate that L-arginine is a potent remedy in reducing blood pressure of young spontaneous hypertensive rats. Overall, a twenty percent (20%) reduction (30 mmHg) of blood pressure was achieved at the maximal dose, whereas no effect was documented in normotensive rats. The L-arginine effect may be mediated via generation of nitric oxide which elicits vasodilation and consequently lowers blood pressure.

EXAMPLE 2

Administration of Heme-L-arginate

Five-week-old male spontaneous hypertensive rats and normotensive Wister Kyoto rats were purchases from Charles River (Wilmington, Mass.) and were fed and housed under identical conditions. Both spontaneous hypertensive rats and Wister Kyoto rats weighed the same at the beginning of the study, 116.3±12.5 g and 120.6±12.0 g, respectively. Forty-five-day-old spontaneous hypertensive rats and Wister Kyoto rats were injected with heme-L-arginate obtained from Leiras-Medica, Finland at 15 or 30 mg/kg body weight intraperitoneally in a final volume of 1.0 ml saline for four consecutive days. The dilution was made just before injection. The control spontaneous hypertensive rats and Wister Kyoto rats were injected with saline. Blood pressure from the tail was measured without anesthesia using a plethysmograph before and 23 hours after the last heme arginate administration.

Control and treated animals were sacrificed in pairs at intervals of 5, 7 and 24 hours after the last heme-L-arginate administration. One kidney from each rat and parts of the liver were immediately frozen in liquid nitrogen for RNA extraction. The remaining control and treated animals were killed 24 hours after the heme-L-arginate treatment. The livers and kidney were perfused with cold saline. Groups of control and treated animals were retained for study of the long-term effect on blood pressure after heme-L-arginate treatment at age 45 to 48 days; blood pressure was measured once a week from 7 to 13 weeks of age.

As seen in Table 1, administration of heme-L-arginate resulted in a marked decrease in blood pressure in 7-week-old spontaneous hypertensive rats (SHR), whereas no significant changes in blood pressure were monitored in age-matched normotensive Wistar Kyoto (WKY). The effect of heme-L-arginate could be detected following the first day of its administration. The maximal effect was achieved by the fourth day of treatment, but started to increase after cessation of heme-L-arginate administration as noted in FIG. 3. Systolic blood pressure was measured by tail cuff plethysmograph before and 24 hours after the last ingestion and then every other week. Results are the means ±SD, n=3 in each group; *p<0.001, p<0.01, and *p<0.05. Furthermore, the heme-L-arginate effect on blood pressure was also evident in 22-week-old spontaneous hypertensive rats. As seen in Table 2, administration of heme-L-arginate at 15 mg and 30 mg/kg body weight for 4 days decreased blood pressure by 7 and 12 mmHg, respectively. Although the heme-L-arginate effect on blood pressure in older spontaneous hypertensive rats was much lower than in younger spontaneous hypertensive rats, i.e., a decrease of blood pressure of 7 mm Hg vs. 26 mmHg for 20- and 7-week-old spontaneous hypertensive rats, respectively, it was significantly different from the controls as noted in Table 2.

Applicants further examined whether the effect is due to heme or to the arginine component of heme arginate. In separate experiments, applicants treated 7-week-old spontaneous hypertensive rats with heme-L-arginate, hemin alone and L-arginine alone at the same dose (15 mg/kg body weight). As seen in Table 3, both heme and L-arginine significantly reduced blood pressure in 7-week-old spontaneous hypertensive rats by 14.3 and 9.7 mmHg, respectively. At the same period, blood pressure in control spontaneous hypertensive rats increased by 7.7 mmHg. However, the effect of heme-L-arginate on blood pressure had a much greater decrease of 21.8 mmHg, which is the sum of the heme and arginine effects as noted in Table 3. Interestingly, when 7-week-old spontaneous hypertensive rats were treated with heme-L-arginate and an inhibitor of heme oxygenase, ZnDPBG (Zn-2,4-deuteropophyrin IX bis glycol), blood pressure decreased by only 14 mmHg. The heme oxygenase inhibitor alone did not have any effect on blood pressure as seen in Table 3.

Administration of heme-L-arginate (15 mg/kg body weight for 4 days) resulted in a marked decrease in blood pressure from 156.3±4.7 to 129.8±4.5 mm Hg (p<0.001), whereas blood pressure in spontaneous hypertensive rats receiving the vehicle control was not affected. In contrast, administration of heme-L-arginate or its vehicle to age-matched Wister Kyoto rats did not influence blood pressure, 119.5±3.3 mm Hg vs. 121.0±2.1 mmHg, respectively.

Applicants also studied the effect of heme-L-arginate, a potent inducer of heme oxygenase, on microsomal cytochrome P-450 levels in spontaneous hypertensive rats at 7 weeks of age.

Heme oxygenase activity was increased in both hepatic and renal microsomes of spontaneous hypertensive rats and Wister Kyoto rats by two to four fold following treatment with heme-L-arginate. The increase in heme oxygenase activity was associated with a parallel decrease in cytochrome P-450 content and in the activity of cytochrome P-450 $\omega/\omega$-1 arachidonate hydroxylases in kidneys of spontaneous hypertensive rats. Expression of the heme oxygenase gene following administration of heme-L-arginate was examined by Northern blot hybridization. Maximal increase of heme oxygenase mRNA occurred 5 to 7 hours after the last injection of heme-L-arginate and returned to control levels after 24 hours.

While not wishing to be bound by any theory, Applicants postulate that heme-L-arginate treatment resulted in induction of heme oxygenase which consequently led to a diminution of cytochrome P-450 especially the arachidonate $\omega/\omega$-1 hydroxylases leading to a marked decrease in 19-HETE and 20-HETE. The effect of heme-L-arginate on blood pressure may be mediated via these biochemical events as both 19-HETE and 20-HETE produced by the kidney may promote hypertension by causing vasoconstriction and sodium retention.

TABLE 1

Effect of Heme-L-Arginate on Systolic Blood Pressure in 7-week-old SHR and WKY

| | Systolic blood pressure | |
|---|---|---|
| | Control (mmHg) | Treated (mmHg) |
| SHR (n = 8) | 156.3 ± 4.7 | 129.8 ± 4.5* |
| WKY (n = 8) | 119.5 ± 3.3 | 121.0 ± 2.1 |

Systolic blood pressure was measured by tail cuff pletysmograph 23 hours after the last heme-L-arginate administration (15 mg/kg body weight/day for 4 consecutive days, i.p.); results are means ±SD; * indicates significance from control, p<0.001.

TABLE 2

| | Systolic Blood Pressure in 22-Week-Old SHR | |
|---|---|---|
| Heme-L-arginate dose | Before treatment (mmHg) | After treatment (mmHg) |
| 15 mg/kg (n = 4) | 193.3 ± 2.1 | 187.5 ± 1.3** |
| 30 mg/kg (n = 3) | 198.1 ± 4.8 | 185.7 ± 4.2* |

Heme-L-arginate was given to 22-week-old spontaneous hypertensive rats (SHR) for 4 consecutive days. Systolic blood pressure was measured by tail cuff pletysmograph before and 20 hours after the last injection. Results are the means ±SD; * indicates significance from control, p<0.005 and ** indicates significance from control, p<0.05.

TABLE 3

| | Systolic Blood Pressure in 7-Week-Old SHR | |
|---|---|---|
| | Before treatment (mmHg) | After treatment (mmHg) |
| Control | 158.4 ± 4.1 | 166.0 ± 2.7 |
| Heme-L-arginate (15 mg hemin, 16 mg L-arginine per kg) | 154.3 ± 1.9 | 132.5 ± 7.3* |
| Hemin (15 mg/kg) | 156.5 ± 3.3 | 142.2 ± 2.4* |
| L-arginine (16 mg/kg) | 154.1 ± 4.5 | 144.4 ± 3.0* |
| Heme-L-arginate + | 160.4 ± 3.8 | 146.5 ± 2.6* |

TABLE 3-continued

| Systolic Blood Pressure in 7-Week-Old SHR | | |
|---|---|---|
| | Before treatment (mmHg) | After treatment (mmHg) |
| ZnDPBG (7 mg/kg) | | |
| ZnDPBG (7 mg/kg) | 154.0 ± 4.0 | 169.1 ± 2.5 |

Systolic blood pressure was measured by tail cuff pletysmograph before and 23 hours after the last injection. Results are the same ±SD, n=5 in each group; significance from control spontaneous hypertensive rats after 4 days of treatment with the vehicle (166.0±2.7), *p<0.005.

While the invention has now been described with reference to several preferred embodiments, those skilled in the art will appreciate that various substitutions, omissions, modifications, and changes may be made without departing from the scope or spirit thereof. Accordingly, it is intended that the foregoing description be considered merely exemplary of the invention and not a limitation thereof.

We claim:

1. A method for treating a high vascular resistance disorder in a mammal, said method comprising administering to a mammalian organism in need of such treatment a sufficient amount of L-arginine or pharmaceutically acceptable salt thereof to treat a high vascular resistance disorder.

2. The method as claimed in claim 1, wherein the high vascular resistance disorder is hypertension.

3. The method as claimed in claim 1, wherein the high vascular resistance disorder is primary or secondary vasospasm.

4. The method as claimed in claim 1, wherein the high vascular resistance disorder is angina pectoris.

5. The method as claimed in claim 1, wherein the high vascular resistance disorder is cerebral ischemia.

6. The method as claimed in claim 1, wherein the high vascular resistance disorder is preeclampsia.

7. The method as claimed in claim 1, wherein L-arginine is present in an amount from about 1 mg to 1500 mg per day.

8. The method as claimed in claim 7, wherein L-arginine is present in an amount from about 10 mg to 400 mg per day.

9. The method as claimed in claim 1, wherein L-arginine is present along with a pharmaceutically acceptable carrier.

10. The method as claimed in claim 1, wherein L-arginine is in the form of L-arginine hydrochloride.

11. The method as claimed in claim 1, wherein L-arginine is adapted for oral administration.

12. The method as claimed in claim 1, wherein L-arginine is formulated as a tablet or capsule.

13. The method as claimed in claim 11, wherein L-arginine is in sustained release form.

14. The method as claimed in claim 1, wherein L-arginine is in parenteral form.

15. The method as claimed in claim 1, wherein L-arginine is suitable for intraperitoneal administration.

16. A method for treating hypertension in a mammal, said method comprising administering to a mammalian organism in need of such treatment about 1 mg to 1500 mg of L-arginine or pharmaceutically acceptable salt thereof.

17. The method as claimed in claim 16, wherein L-arginine is suitable for oral administration.

18. The method as claimed in claim 16, wherein L-arginine is suitable for parenteral administration.

19. The method as claimed in claim 16, wherein L-arginine is in the form of L-arginine hydrochloride.

* * * * *